United States Patent [19]

Juliano et al.

[11] 4,014,995

[45] Mar. 29, 1977

[54] COSMETICS CONTAINING FINELY DIVIDED OAT FLOUR

[75] Inventors: Angelo L. Juliano, Chicago; Aaron Miller, Northbrook, both of Ill.

[73] Assignee: The Quaker Oats Company, Chicago, Ill.

[22] Filed: Apr. 7, 1975

[21] Appl. No.: 565,695

Related U.S. Application Data

[63] Continuation of Ser. No. 398,651, Sept. 19, 1973, abandoned.

[52] U.S. Cl. .................................. 424/168; 424/63; 424/64; 424/65; 424/68; 424/69; 424/70; 424/71; 424/74; 424/195; 424/364

[51] Int. Cl.² .................. A61K 31/00; A61K 47/00

[58] Field of Search ............. 424/69, 168, 364, 195

[56] References Cited

UNITED STATES PATENTS

| | | | |
|---|---|---|---|
| 1,550,026 | 8/1925 | Goode | 424/195 |
| 1,995,663 | 3/1935 | Bollmann | 424/69 |
| 2,436,818 | 3/1948 | Musher | 424/71 X |

*Primary Examiner*—Leonard Schenkman
*Attorney, Agent, or Firm*—Neuman, Williams, Anderson & Olson

[57] ABSTRACT

Improved cosmetic preparations are obtained by inclusion of a particular oat flour.

5 Claims, No Drawings

COSMETICS CONTAINING FINELY DIVIDED OAT FLOUR

This is a continuation of application Ser. No. 398,651 filed Sept. 19, 1973, now abonadoned. The present invention relates to improvements in cosmetic preparations.

A wide variety of cosmetic preparations are available, and the cosmetic industry is constantly striving to improve cosmetics from both functional and aesthetic standpoints.

Accordingly, it is a principal object of this invention to provide improvements in cosmetic formulations.

It is a particular object of the invention to provide liquid and/or solid containing cosmetic preparations which also contain particulate solid material in a form desired for application to the skin.

The pesent invention involves the discovery that oat flour of a defined particle size can be advantageously incorporated in cosmetic formulations to impart various desirable attributes such as, for example, absorbency, and to give a smooth feeling and look to the skin. The particulate oat flour possesses requisite adhesiveness so that it clings to the skin upon evaporation of volatile components of the cosmetic formulation.

The oat flour which has been found to be particularly useful in cosmetic preparations in accordance with this invention is a finely divided material having a particle size such that more than 98% passes through a 200 mesh screen (U.S. Sieve Series), and preferably at least about 95% will pass through a 325 mesh screen. The flour is used in cosmetic formulations in amounts of from about 1 to 20% or more of the formulation by weight. This particulate oat flour can be characterized as forming colloidal dispersions in solvents and because of this remains suspended in liquid vehicles for extended periods of time. This special oat flour is obtained by grinding oat flakes in conventional manner followed by air classification to obtin the desired particulate material. On a dry basis this oat flour is relatively high in starch content (generally >70%) and lipid content (generally 7.6%) and relatively low in gum, ash (generally <2.5%) and fiber (generally <0.6%) and has a protein content generally of about 16% or less with the protein not being substantially disrupted as would be the case if the flour were obtained by repeated grinding, screening or bolting operations.

The special oat flour can be used advantageously in a very broad range of cosmetic preparations. The oat flour exhibits compatibility with the ionic and nonionic materials usually employed for emulsification purposes, it disperses readily in a variety of liquid solvents and undergoes hydration in water to which it imparts increases in apparent viscosity. In emulsion systems containing a quantity of oil, the flour poses no processing problems, and results in cosmetic preparations which are eminently satisfactory from a cosmetic standpoint. The special oat flour can be successfully incorporated into such cosmetic preparations as hand lotions and creams to create an aesthetically elegant system possessing the conditioning effects of protein and the emollient and moisturizing properties of hydrophobic lipid materials. The oat flour can be directly incorporated into the aqueous phase of such systems prior to any heating operation, if any is required.

Moisturizing creams and lotions can be formulated with the oat flour, which functions along with other lubricants and emollients to impart a soft, smooth residual feel to the skin. Night creams and lotions can be compounded with the special oat flour. These systems can be formulated to achieve pH values which approximate those of normal skin. Since the oat flour is compatible with various ingredients of cosmetic formultions, it is possible to design products having pH values of approximately 5.5 (approximate skin pH). Since washing with soaps or other alkaline cleansing materials usually alters the normal acid mantle of the skin, use of formulations designed to approximate the normal skin pH can help soothe a rough, dry, chapped epidermis. The physical presence of oat flour on the skin after evaporation of relatively volatile formulation ingredients, such as water or alcohols, provides a highly desirable skin feel.

The use of oat flour in under-makeup moisturizing creams and lotions can provide these products with not only the desirable attributes of moisturizing, but the flour helps makeup of various types adhere to the surface of the skin. Since oat flour contains whole protein, which is a polymer-like material, it is postulated that this desirable attribute relates to this as well as other constituents in the flour. This means a reduced necessity for makeup to be reapplied during the course of the day. Furthermore, the flour, by virtue of its oil and water adsorption characteristics, helps keep the makeup from streaking or discoloring due to perspiration or oils which are found on the surface of the epidermal layer.

For the most part, cleansing lotions and creams are emulsion systems containing a quantity of oils which vary between 15 and 50% by weight. These systems are designed to remove many cosmetic preparations, such as lipstick, facial makeup and eye makeup, by virtue of solvent and emulsifying mechanisms. In some instances products are formulated so that they can be removed from the face after the cleansing operation by water. In other cases, these formulations must be tissued off after they have been used to remove various cosmetics. In any case, they provide a cleansing function which varies from that imparted by soap. These systems can be designed to approximate the pH of the normal epidermis, unlike most soaps which tend to be somewhat alkaline in response. Furthermore, these lotions and creams are less prone to emulsify and remove lipids normally found on the surface of the epidermal layer, thus defatting and possibly making the skin more prone to irritation.

Oat flour can be incorporated into cleansing lotions and creams not only to impart a skin conditioning effect by virtue of its protein content, but it offers moisturizing properties due to the presence of lipids. Cleansing creams and lotions not only offer bland effective removal of "make-ups," environmental residue, such as dust and dirt, but they offer an excellent method of lubricating and moisturizing dry skin. Oat flour can be incorporated into cleansing creams and lotions for the individual who finds this method of cleaning more acceptable than soap.

Oat flour in anhydrous bath oils enhances the positive attributes of lubricating, moisturizing and emolliency related to the oils, such as mineral oil, lanolin derivatives or fatty acids used in these products. Furthermore, the dermatological attributes inherent in the oat flour due to the protein and lipid content further supplements the effect of the anhydrous bath oil.

Addition of this special oat flour, due to its emollient characteristics, aids in relieving skin irritation which may develop while not affecting the foam characteristic of the bath oils.

Massage lotions and creams can be designed to embody a number of useful attributes if oat flour is used as one of the formulation ingredients. The system can be designed so that the normal epidermal acid mantle is approximated. This can be achieved by using formulation ingredients, such as nonionic emulsifying agents, which will permit the inclusion of substances used to maintain a hydrogen ion concentration relted to a pH of about 5.5. The use of oat flour in situations requiring this pH does not cause any formulation related compatibility problems.

Oat flour can also contribute to the stability of these emulsions by virtue of effect on the apparent viscosity of these systems as well as solubility characteristics. Oat flour appears to have hydrophilic (water loving) as well as lipophilic groups which are postulated to give the flour value as an emulsifier. Obviously, the conditioning effects of protein can serve a role in enhancing the functional characteristics of massage related products. The presence of fat in the flour offers moisturizing effects.

The use of protein in shampoos and the marketing success of these products is well known. However, the so-called protein used in these products are usually hydrolyzed collagen which contains amino acids, polypeptides and other protein residues. In the case of oat flour, the protein found in this material is unhydrolyzed and therefore whole. Oat flour contains lipids which is also true of the surface of the scalp. These lipids help impart a healthy luster to the hair fiber. Furthermore, they can lubricate the cuticle layer of the fiber so that these cells will easily move past the cells from adjacent fibers, thus facilitating combing. Oat flour can be incorporated into shampoos without adversely affecting foam characteristics.

Shampoos can be formulated in the form of creams and liquids. In the case of liquids, these can be low to moderate in apparent viscosity. The oat flour is suitable for use in any of these products, however, the method of incorporating the material will vary. In the case of liquid shampoos of low to moderate viscosity, the oat flour can be incorporated most simply by making an aqueous dispersion of the flour.

In the case of hair conditioners, the use of the oat flour is advantageous by virture of its protein and lipid content. Hair conditoners are normally used as a treatment, for those individuals whose hair has been damaged through the use of hair dyes, hair waving formulations, hot combs, tints and other procedures normally associated with damage to the cuticle or protein of the hair fiber. Injury to the cuticle can and often does manifest itself as unsightly split ends, while damage to the protein of the fiber, being more serious, can manifest itself as hair breakage and loss. Treatments containing proteins and other lipid conditioners are often used in an attempt to obviate these undesirable conditions. Usually a conditioner use is a palliative measure in that the problem is not usually corrected, but the fiber through the use of conditioning products continues to grow producing new undamaged fiber. Some investigators have suggested, through the use of devices designed to measure the tensile strength of fibers, that hair conditioners containing protein can increase the strength of individual fibers. From an aesthetic standpoint, the use of conditioners containing protein as well as substantiative agents such as specific cationic materials, can leave the hair more lusterous, manageable, softer and sometimes thicker appearing. The use of oat flour in formulas of this type provides whole protein derived from a "natural" source as well as lipids.

Hair sprays and setting aids contain for the most part high polymers as hair "holding" ingredients. Formulas containing these materials are designed by the formulator to offer various holding characteristics which will affect the hair by imparting a relatively stiff to soft natural curl. It is possible through the incorporation of various ingredients, such as plasticizers and neutralizing agents, in those systems containing carboxy functional group resins, to alter the firmness of the set while maintaining holding characteristics under adverse environmental conditions, such as high humidity. The use of oat flour as a resin modifier offers the formulator a material in hydroalcoholic systems which contains protein which serves to condition the hair as well as lipids which can help impart sheen. The natural origin of the flour, as well as its protein content, make it particularly well suited for products of this type.

Face masks are frequently used to help treat various undesirable epidermal related conditions. They can be used in the treatment of oily skin to impart lipid adsorbent effect. They are sometimes used to help suppress wrinkles by embodying an astringent effect. They are sometimes used to treat acne and other concomitant adolescent or hyperactive sebaceous gland related problems by incorporating antibacterial agents as well as auxiliary astringents such as aluminum phenolsulfonate. In addition to absorbing excess oils, this naturally derived flour with its protein content makes it particularly well suited in products of this type.

Cleansing scrubs vary widely in their form and functions. The scrub can take the form of a moderately viscous liquid containing a quantity of synthetic surface active material which is used to thoroughly cleanse the skin. The cleansing effect in this case is due to the colloidal character, wetting emulsifying and dispersing effect of the surface active material. This type of product is suitable for "oily skin" but may cause epidermal irritation in some individuals. The use of oat flour in scrubs of this type can help reduce the epidermal defatting and possible concomitant irritation without sacrificing cleansing effectiveness. These scrubs can also contain various antibacterials, such as Hexachlorophene, for the purpose of eliminating various organisms found on the surface of the skin. The use of these antibacterial agents can produce a source of additional epidermal irritation which is reduced through the inclusion of oat flour.

Cleansing scrubs can also take the form of dispersion of various insoluble solid materials such as almond meal in polyhydric alcohols such as glycerine or propylene glycol. These not only offer solvent (glycol) related cleaning, but the solid insoluble matter acts to gently massage the skin as well as enhance the cleansing process. The inclusion of oat flour in formulas based on the dispersion of various insoluble solid materials in polyhydric alcohols provides product attributes related to the protein and lipid content of the flour. The flour will assist in the skin cleansing operation by means of the residue removal effect created by massaging with the glycol dispersed oat flour.

Skin fresheners are, as the name implies, used to produce a refreshing and cooling sensation after a bath or shower or during the course of the day. Skin fresheners can function to assist in the removal of makeup by virtue of their solvent attributes in which capacity they also impart a cooling sensation and sometimes a skin tightening effect. Fresheners or toiletries such as after shave lotions can also be used as vehicles for the application of fragrance, deodorant, astringent and lubricating characteristics to a number of areas of the body, hands and face. They can be applied in conjuction with daily personal care routines, such as bathing or showering. They can also be used during the course of the day to impart the attributes mentioned, as well as a cooling and refreshing effect.

It has heretofore been recognized that it would be highly desirable to incorporate talcum powder into skin freshening compositions which involve a liquid vehicle, such as those containing alcohol or alcohol and water. This is because talcum powder absorbs moisture and leaves the skin soft and smooth to the touch.

Heretofore, attempts to incorporate talcum or related materials have met with serious formulation difficulties. Incorporation of talcum and related ingredients, such as magnesium silicate, calcium carbonate, magnesium carbonte and/or zinc stearate in such systems usually result in sedimentation of these solids because of their poor hydration characteristics in the suspending vehicle. Even by using the so-called suspending or dispersing agents, such as high polymers or surface active materials, it is difficult to uniformly disperse these materials so that when the freshener is used, the powder related ingredients will be unevenly applied. A non-uniform layer of the powder related materials is deposited and white areas of high concentrations are visible. Obviously, the aesthetics of such a situation are unacceptable. The use of special oat flour in products of this type enhances the functional attributes of the formulation, not only because of the protein and lipids therein, but also because of the smooth, velvety residual skin characteristics imparted after the solvents, such as water and alcohol, have evaporated.

The following numbered examples illustrate representative cosmetic formulations embodying the discovery of the present invention, their preparation and attributes. The special oat flour employed in these examples is the particulate oat flour as described heretofore.

EXAMPLE 1

| PIGMENTED SYSTEMS SKIN TINT | ATTRIBUTES: MOISTURIZING CONDITIONING OIL/WATER ANIONIC SYSTEMS FOR USE UNDER MAKEUP TO IMPART MORE NATURAL SKIN TONE. |  |
|---|---|---|
| INGREDIENT |  | % W/W |
| 1. Myvacet type 9-40 |  | 0.25 |
| 2. Stearic Acid (triple pressed) |  | 3.5 |
| 3. Glyceryl Monostearate (non self emulsifiable) |  | 1.7 |
| 4. Lanolin (cosmetic grade) |  | 2.0 |
| 5. Mineral Oil (65/75 Saybolt) |  | 8.0 |
| 6. Propylparaben |  | 0.1 |
| 7. Methylparaben |  | 0.1 |
| 8. Special Oat Flour |  | 1.5 |
| 9. Deionized Water | QS | 100.00 |
| 10. Propylene Glycol |  | 3.0 |
| 11. Titanium Dioxide |  | 2.0 |
| 12. Red No. 2513 |  | 0.9 |
| 13. Ultra Blue 3585 |  | 0.2 |
| 14. Triethanolamine |  | 1.0 |
| 15. Dowicil 200 |  | 0.1 |
| 16. Perfume |  | QS |

COMPOUNDING PROCEDURE

Weigh No. 1 - No. 6 and heat, 70°-73° C., while stirring continuously.

Weigh No. 7 - No. 10 and heat to 70°-73° C.; add this to the heated oil.

Phase components (both phases should be at 70°-73° C.)

Add No. 11, No. 12 and No. 13 and mix until uniformly dispersed.

Add No. 14, cool to 35°-40° C. and add No. 15 and No. 16. Fill at 25°-30° C.

EXAMPLE 2

| PIGMENTED SYSTEMS SKIN TINT | ATTRIBUTES: MOISTURIZING CONDITONING OIL/WATER ANIONIC/NONIONIC EMULSION SYSTEM FOR USE UNDER MAKEUP TO IMPART MORE NATURAL SKIN TONE. |  |
|---|---|---|
| INGREDIENT |  | % W/W |
| 1. Lantrol |  | 0.3 |
| 2. Stearic Acid (triple pressed) |  | 3.25 |
| 3. Polawax |  | 1.5 |
| 4. Mineral Oil (65/75 Saybolt) |  | 6.0 |
| 5. Propylparaben |  | 0.10 |
| 6. Methylparaben |  | 0.10 |
| 7. Special Oat Flour |  | 2.0 |
| 8. Deionized Water | QS | 100.00 |
| 9. Propylene Glycol |  | 4.0 |
| 10. Titanium Dioxide |  | 2.0 |
| 11. Lo Micron Pink No. 2511 |  | 0.7 |
| 12. Yellow No. 2576 |  | 0.3 |
| 13. Red No. 2513 |  | 0.1 |
| 14. Dowicil 200 |  | 0.10 |

EXAMPLE 2-continued

| PIGMENTED SYSTEMS SKIN TINT | ATTRIBUTES: MOISTURIZING CONDITIONING OIL/WATER ANIONIC/NONIONIC EMULSION SYSTEM FOR USE UNDER MAKEUP TO IMPART MORE NATURAL SKIN TONE. |
|---|---|
| INGREDIENT | % W/W |
| 15. Perfume | QS |
| 16. Triethanolamine | 1.0 |

COMPOUNDING PROCEDURE

Weigh the oil phase No. 1 - No. 5; commence stirring and heating.
Heat to 70°–73° C. Weigh No. 6, No. 7, No. 8 and No. 9 and heat while stirring to 70°–73° C. Add the "aqueous" phase to the oil phase. Continue stirring and add No. 10, No. 11, No. 12 and No. 13.
Stir until a uniform dispersion results. Add No. 16. Cool to 35°–40° C. Add No. 14 and No. 15. Fill at 25°–30° C.

COMPOUNDING PROCEDURE

Weigh phase A(No. 1 - No. 10) and begin heating and stirring. Heat to approximately 80° C. and mix until all waxes have melted. Prepare part B several hours in advance by adding No. 1 - No. 3 to No. 4 and processing by means of a roller mill. Cool part A to 70°–73° C. and add No. 11 and part B (No. 12). Mix thoroughly and pour into molds.

EXAMPLE 3

| | PIGMENTED SYSTEMS LIPSTICK | ATTRIBUTES: APPLIES UNIFORMLY, EMOLLIENT AND LUBRICATING GOOD "SLIP". | |
|---|---|---|---|
| | INGREDIENT | | % W/W |
| A | 1. Candelila Wax | | 5.0 |
| | 2. Carnauba Wax | | 2.0 |
| | 3. Ceresin Wax | | 1.5 |
| | 4. Emerwax 4226-0 | | 1.5 |
| | 5. Cetiol V | | 4.0 |
| | 6. Mineral Oil (65/75 Saybolt) | QS | 100.00 |
| | 7. Beeswax | | 8.0 |
| | 8. Lanolin (Cosmetic Grade) | | 10.0 |
| | 9. Amerlate P | | 10.0 |
| | 10. Viscolan | | 5.0 |
| | 11. Special Oat Flour | | 2.0 |
| | 12. Pigments | | 47.0 |

| | PIGMENT FORMULA INGREDIENT | PARTS BY WEIGHT |
|---|---|---|
| B | 1. Titanium Dioxide | 7.0 |
| | 2. D&C Red No. 21 | 1.25 |
| | 3. D&C Red No. 7 | 1.5 |
| | 4. Castor Oil | 40.25 |

EXAMPLE 4

| PIGMENTED SYSTEMS LIPSTICK | ATTRIBUTES: EXCELLENT SLIP LUBRICITY, GOOD COVERAGE | |
|---|---|---|
| INGREDIENT | | % W/W |
| 1. Candelia Wax | | 5.00 |
| 2. Carnauba Wax | | 2.00 |
| 3. Ozocerite | | 1.50 |
| 4. Emerwax 4266-0 | | 1.50 |
| 5. Cetiol V | | 4.00 |
| 6. Mineral Oil (65/75 Saybolt) | | 5.00 |
| A | | |
| 7. Beeswax | | 8.00 |
| 8. Lanolin (Cosmetic Grade) | | 10.00 |
| 9. Castor Oil | QS | 100.00 |
| 10. Special Oat Flour | | 2.00 |
| 11. Color Pigments | | 47.00 |

| PIGMENT FORMULA | |
|---|---|
| INGREDIENT | PARTS BY WEIGHT |
| 1. Titanium Dioxide | 8.00 |
| 2. D&C Red No. 19 | 2.25 |
| B | |
| 3. D&C Red No. 21 | 1.50 |

EXAMPLE 4-continued

| | |
|---|---|
| 4. Castor Oil | 35.25 |

COMPOUNDING PROCEDURE

Weigh phase A (No. 1 - No. 9) and begin heating and stirring. Heat to approximatly 80° C. and mix until all waxes have melted. Prepare part B several hours in advance by adding No. 1 - No. 3 to the castor oil and processing with a roller mill. Cool part A to 70°-73° C. and add No. 10 and part B (No. 11). Mix thoroughly and pour into molds.

EXAMPLE 5

| PIGMENTED SYSTEMS MAKEUP CREAM | ATTRIBUTES: MOISTURIZING, GOOD COVERAGE OIL/WATER EMULSION ANIONIC IN NATURE |
|---|---|
| INGREDIENT | % W/W |
| 1. Avacado Oil | 4.0 |
| 2. Lanolin (Cosmetic Grade) | 2.00 |
| 3. Stearic Acid (triple pressed) | 4.00 |
| 4. Glyceryl Monostearate (non self emulsifying) | 5.00 |
| 5. Stearyl Alcohol | 2.00 |
| 6. Mineral Oil (65/75 Saybolt) | 4.00 |
| 7. Cetiol V | 5.00 |
| 8. Propylparaben | 0.10 |
| 9. Methylparaben | 0.10 |
| 10. Triethanolamine | 1.00 |
| 11. Propylene Glycol | 5.00 |
| 12. Dowicil 200 | 0.10 |
| 13. Special Oat Flour | 2.00 |
| 14. Deionized Water QS | 100.00 |
| 15. Perfume | QS |
| 16. Titanium Dioxide | 3.50 |
| 17. Lo Micron Brown 2593 | 1.30 |
| 18. Lo Micron Pink 2511 | 0.30 |
| 19. Lo Micron Yellow 2576 | 0.20 |

COMPOUNDING PROCEDURE

Weigh the "oil" phase (ingredients No. 1 - No. 8) begin heating and stirring. Weigh No. 13, No. 14, No. 9 and No. 11 and begin heating and stirring. Add the aqueous phase to the oil phase. Continue stirring. Add pigments No. 16, No. 17, No. 18 and No. 19. Mix until the pigment is homogeneously dispersed. Add No. 10. Cool to 35°-40° C. and add No. 12 and No. 15. Fill at 25°-30° C.

EXAMPLE 6

| PIGMENTED SYSTEMS EYE SHADOW | ATTRIBUTES: UNIFORM COVERAGE, EMOLLIENT ANIONIC OIL/WATER EMULSION, GOOD ADHESION |
|---|---|
| INGREDIENT | % W/W |
| 1. Mineral Oil (65/75 Saybolt) | 8.0 |
| 2. Amerlate P | 2.0 |
| 3. Stearic Acid (Triple pressed) | 4.0 |
| 4. Glyceryl Monostearate (non self emulsifying) | 5.0 |
| 5. Cetyl Alcohol | 2.0 |
| 6. Cetiol V | 5.0 |
| 7. Propylparaben | 0.10 |
| 8. Methylparaben | 0.10 |
| 9. Special Oat Flour | 1.0 |
| 10. Triethanolamine | 1.0 |
| 11. Propylene Glycol | 5.0 |
| 12. Dowicil 200 | 0.10 |
| 13. Deionized Water QS | 100.00 |
| PIGMENTS | |
| 1. Chromalite Dark Blue | 3.5 |
| A  2. Chromalite Magenta | 2.0 |
| 3. Pearl Glow | 5.0 |

COMPOUNDING PROCEDURE

Weigh the "oil" phase ingredients (No. 1 - No. 7) begin heating and stirring. Heat to 70°-73° C. Weigh No. 13, No. 11, No. 9 and No. 8 into another container and begin stirring and heating. Heat to 70°-73° C. Add the aqueous phase components which are at 70°-73° C. to the oil phase component. Add part A and mix until the pigments are uniformly blended. Add No. 10 and cool to 35°-40° C. at which temperature add No. 12. Fill at 25°-30° C.

EXAMPLE 7

| SKIN TREATMENT RELATED FORMULATIONS FACIAL SCRUB | ATTRIBUTES: SOLVENT CLEANING EFFECT, ABSORBENT, CONDITIONING, MASSAGE ATTRIBUTE DUE TO INSOLUBLE MATERIALS. |
|---|---|

| INGREDIENT | | % W/W |
|---|---|---|
| 1. Propylene Glycol | | 17.500 |
| 2. Sorbitol | | 17.500 |
| 3. Methylparaben | | 0.100 |
| 4. Special Oat Flour | | 15.000 |
| 5. Zinc Oxide | | 10.000 |
| 6. Talc | | 20.000 |
| 7. Sorbic Acid | | 0.100 |
| 8. Formaldehyde Solution | | 0.075 |
| 9. Deionized Water | QS | 100.00 |
| 10. Perfume | | QS |
| 11. Color | | QS |

COMPOUNDING PROCEDURE

Weigh in order No. 1 - No. 10 while stirring continuously. Mix for about 1.5 hours after all ingredients have been added and continue mixing while filling.

EXAMPLE 8

| SKIN TREATMENT RELATED FORMULATIONS MUD PACK | | |
|---|---|---|

| INGREDIENT | | % W/W |
|---|---|---|
| 1. Sorbitol | | 5.000 |
| 2. Deionized Water | QS | 100.000 |
| 3. Methylparaben | | 0.100 |
| 4. Fullers Earth | | 30.000 |
| 5. Special Oat Flour | | 5.000 |
| 6. Dowicil 200 | | 0.075 |

COMPOUNDING PROCEDURE

Weigh No. 1, No. 2, No. 3 and No. 6 into a container and commence stirring. Add No. 4 and No. 5 and stir until a smooth homogeneous paste results.

EXAMPLE 9

| SKIN TREATMENT RELATED FORMULATIONS PEEL OFF MASK | ATTRIBUTES: ASTRINGENT, CONDITIONING SOFTENS AND SMOOTHS THE SKIN, HELPS REDUCE THE APPEARANCE OF WRINKLES. |
|---|---|

| INGREDIENT | | % W/W |
|---|---|---|
| 1. Special Oat Flour | | 5.00 |
| 2. Gelvatol 3/90 | | 10.00 |
| 3. Deionized Water | QS | 100.00 |
| 4. Glycerine | | 1.00 |
| 5. Resyn 2260 | | 5.00 |
| 6. Ethyl Alcohol SDA No. 40 | | 16.00 |
| 7. 2-Amino-2-Methyl-1,3-Propanediol | | 0.02 |
| 8. Color | | QS |
| 9. Perfume | | QS |

COMPOUNDING PROCEDURE

Weigh No. 3 and add while stirring continuously No. 1 and No. 2. Heat to 70°–73° C., begin cooling after mixing for 15 minutes at this temperature. Continue stirring and add NO. 4 and No. 5 at 50°–54° C. and No.6. Continue stirring and cooling and add No. 7, No. 8 and No. 9 at 25°–30° C.

EXAMPLE 10

| SKIN TREATMENT RELATED FORMULATIONS FACE AND BODY SHAMPOO | ATTRIBUTES: CONDITIONING EMULSIFIES AND DISPERSES UNDESIRABLE EPIDERMAL MATERIALS SUCH AS MAKEUP DUST AND DIRT, GOOD FOAMING CHARACTERISTICS |
|---|---|

| INGREDIENT | | % W/W |
|---|---|---|
| 1. Standapol SH-100 | | 50.00 |
| 2. Standamid SD | | 4.00 |
| 3. Deionized Water | QS | 100.0 |
| 4. Special Oat Flour | | 1.00 |
| 5. Propylene Glycol | | 3.00 |
| 6. Perfume | | QS |
| 7. Color | | QS |
| 8. Dowicil 200 | | 0.10 |

COMPOUNDING PROCEDURE

Weight No. 1 - No. 5 into a tank, begin heating and stirring. Heat to 60°–63° C. while stirring carefully to prevent air entrapment. Stir until the resultant dispersion is uniform. Cool to 35°–40° C. and add No. 8. Cool to 25°–30° C. and add No. 6 and No. 7.

EXAMPLE 11

| SKIN TREATMENT RELATED FORMULATIONS FACIAL MASK | ATTRIBUTES: ASTRINGENT, CONDITIONING PRODUCES A COOLING SENSATION WHEN APPLIED. WASHES OFF EASILY WITH WATER. | |
|---|---|---|
| INGREDIENT | | % W/W |
| 1. Deionized Water | QS | 100.00 |
| 2. Veegum | | 10.00 |
| 3. Special Oat Flour | | 4.00 |
| 4. Methylparaben | | 0.10 |
| 5. Dowicil 200 | | 0.10 |
| 6. Ethyl Alcohol (SDA No. 40) | | 18.00 |
| 7. Color | | QS |
| 8. Perfume | | QS |

COMPOUNDING PROCEDURE

Weigh No. 1 and begin stirring. Add No. 2 and mix until the resultant dispersion is smooth and lump free. Add No. 3, No. 4, No. 5, No. 6, No. 7 and No. 8. Continue mixing until the dispersion is smooth.

EXAMPLE 12

| SKIN CARE HAND AND BODY LOTION | ATTRIBUTES: ANIONIC, MOISTURIZING, NON-GREASY |
|---|---|
| INGREDIENT | % W/W |
| 1. Stearic Acid | 3.00 |
| 2. Cetyl Alcohol | 0.50 |
| 3. Mineral Oil (65/75 Saybolt) | 7.00 |
| 4. Methylparaben | 0.10 |
| 5. Propylparaben | 0.10 |
| 6. Deionized Water  QS | 100.00 |
| 7. Special Oat Flour | 1.00 |
| 8. Triethanolamine | 1.00 |
| 9. Propylene Glycol | 5.00 |
| 10. Dowicil 200 | 0.10 |
| 11. Perfume | QS |

EXAMPLE 12-continued

| SKIN CARE HAND AND BODY LOTION | ATTRIBUTES: ANIONIC, MOISTURIZING, NON-GREASY |
|---|---|
| INGREDIENT | % W/W |
| 12. Color | QS |

COMPOUNDING PROCEDURE

Weigh ingredients Nos. 1, 2, 3, 4 and 5 and heat while stirring to approximately 72° C. In another container weigh No. 6, No. 7, No. 8 and No. 9 and heat while stirring to 72° C. Add the water "phase" to the oil phase and cool, while stirring, to about 40° C. at which temperature No. 10, No. 11 and No. 12 should be added.

EXAMPLE 13

| SKIN CARE HAND AND BODY CREAM | ATTRIBUTES: ANIONIC, MOISTURIZING, NON-GREASY. CAN BE USED FOR MASSAGE PURPOSES. | |
|---|---|---|
| INGREDIENT | | % W/W |
| 1. Stearic Acid (Triple pressed) | | 4.00 |
| 2. Emerwax 4266D | | 4.00 |
| 3. Fluid E370 | | 5.00 |
| 4. Mineral Oil (65/75 Saybolt) | | 5.00 |
| 5. Propylparaben | | 0.10 |
| 6. Methylparaben | | 0.10 |
| 7. Deionized Water | QS | 100.00 |
| 8. Dowicil 200 | | 0.10 |
| 9. Special Oat Flour | | 1.00 |
| 10. Triethanolamine | | 1.00 |
| 11. Perfume | | QS |

COMPOUNDING PROCEDURE

Weigh ingredients No. 1 - No. 6 into a container and heat while stirring, to about 72° C. Weigh No. 7, No. 9 and No. 10 into a separate contianer and heat these while stirring to 72° C. Add the water phase components to the oil phase and cool to about 40° C. Add No. 8 and No. 11. Fill at 25°–30° C.

EXAMPLE 14

| SKIN CARE HAND AND BODY LOTION | ATTRIBUTES: NONIONIC, MOSTURIZING EMOLLIENT NON-GREASY. pH OF APPROXIMATELY 7. | |
|---|---|---|
| INGREDIENT | | % W/W |
| 1. Promulgen | | 4.00 |
| 2. Mineral Oil (65/75 Saybolt) | | 8.00 |
| 3. Cetyl Alcohol | | 1.50 |
| 4. Propylparaben | | 0.10 |
| 5. Methylparaben | | 0.10 |
| 6. Deionized Water | QS | 100.00 |
| 7. Special Oat Flour | | 1.00 |
| 8. Propylene Glycol | | 5.00 |

EXAMPLE 14-continued

| SKIN CARE HAND AND BODY LOTION | ATTRIBUTES: NONIONIC, MOSTURIZING EMOLLIENT NON-GREASY. pH OF APPROXIMATELY 7. |
|---|---|
| INGREDIENT | % W/W |
| 9. Dowicil 200 | 0.10 |
| 10. Perfume | QS |
| 11. Color | QS |

COMPOUNDING PROCEDURE

Weigh ingredients No. 1 - No. 4 into a container and heat to 70°–73° C. while stirring continuously. In another container weigh No. 5, No. 6, No. 7 and No. 8; commence heating while stirring continuously. Heat to 70°–73° C. and then add this emulsion phase (water phase) to the oil phase which should also be at a temperature of 70°–73° C. Stirring should be undertaken when joining the two phases with a high shear mixing apparatus.

EXAMPLE 15

| SKIN CARE SKIN FRESHENER | ATTRIBUTES: COOLING, IMPARTS SKIN CONDITONING AND MOISTURIZING EFFECTS. | |
|---|---|---|
| INGREDIENT | | % W/W |
| 1. Special Oat Flour (2% Dispersion in Deionized Water) | | 50.00 |
| 2. Carbopol 940 (2% Dispersion in Deionized Water) | | 7.50 |
| 3. Triethanolamine | | 0.20 |
| 4. Allantoin | | 0.10 |
| 5. Dowicil 200 | | 0.10 |
| 6. Methylparaben | | 0.10 |
| 7. Propylene Glycol | | 3.00 |
| 8. Deionized Water | QS | 100.00 |
| 9. Perfume | | QS |
| 10. Color | | QS |
| 11. Alcohol SDA No. 40 | | 25.00 |

COMPOUNDING PROCEDURE

Heat No. 1 to approximately 63° C. while stirring continuously, add No. 4, No. 6, No. 7, No. 8 and No. 2. Continue stirring and cool the batch to approximately 40° C. and add No. 5, No. 9, No. 10 and No. 11.

EXAMPLE 16

| SKIN CARE CLEANING CREAM | ATTRIBUTES: CONDITIONING, MOISTURIZING, LUBRICATING. EXCELLENT MAKEUP REMOVAL CHARACTERISTICS. | |
|---|---|---|
| INGREDIENT | | % W/W |
| 1. Beeswax (USP) | | 14.00 |
| 2. Lanolin (Cosmetic Grade) | | 10.00 |
| 3. Mineral Oil (65/75 Saybolt) | | 40.00 |
| 4. Glyceryl Monostearate (self emulsifying) | | 1.25 |
| 5. Polawax | | 0.50 |
| 6. Deionized Water | QS | 100.00 |
| 7. Borax | | 1.30 |
| 8. Methylparaben | | 0.10 |
| 9. Perfume | | QS |
| 10. Color | | QS |
| 11. Special Oat Flour | | 1.50 |

COMPOUNDING PROCEDURE

Weigh ingredients No. 1, No. 2, No. 3, No. 4 and No. 5 into a container and heat while stirring to approximately 72° C. Weigh ingredients No. 6, No. 7 and No. 8 into a container and heat to 72° C. while stirring. At 72° C. and No. 11 and add the water phase of the emulsion to the oil phase while stirring. Cool to about 40° C.; perfume and color. Fill at 25°–30° C.

EXAMPLE 17

| SKIN CARE MOISTURIZING LOTION | ATTRIBUTES: EMOLLIENT LUBRICATING, APPROXIMATELY NEUTRAL pH, DESIRABLE NON-GREASY "FEEL". |
|---|---|
| INGREDIENT | % W/W |
| 1. Polawax | 2.25 |
| 2. Stearyl Alcohol | 2.50 |

EXAMPLE 17-continued

| SKIN CARE MOISTURIZING LOTION | ATTRIBUTES: EMOLLIENT LUBRICATING, APPROXIMATELY NEUTRAL pH, DESIRABLE NON-GREASY "FEEL". | |
|---|---|---|
| INGREDIENT | | % W/W |
| 3. Mineral Oil (65/75 Saybolt) | | 12.00 |
| 4. Cetiol V | | 2.00 |
| 5. Methylparaben | | 0.10 |
| 6. Propylparaben | | 0.10 |
| 7. Deionized Water | QS | 100.00 |
| 8. Special Oat Flour | | 2.00 |
| 9. Glycerine | | 5.00 |
| 10. Carbopol 940 | | 0.10 |
| 11. Triethanolamine | | |
| 12. Dowicil 200 | | 0.10 |
| 13. Color | | QS |
| 14. Perfume | | QS |

COMPOUNDING PROCEDURE

Weigh ingredients No. 1 - No. 6 and commence stirring while heating to about 72° C. In a separate container add No. 10 to No. 7 while mixing continuously, then weigh and add No. 8 and No. 9. Heat the water phase while stirring continuously to about 72° C. and add to the oil phase which is also at this temperature. Add No. 11 continue mixing and cool the batch to about 40° C. at which temperature add No. 12, No. 13 and No. 14. Fill at 25°-30° C.

EXAMPLE 18

| SKIN CARE MOISTURIZING LOTION | ATTRIBUTES: EMOLLIENT LUBRICATING, APPROXIMATELY NEUTRAL pH, DESIRABLE AFTER "FEEL". | |
|---|---|---|
| INGREDIENT | | % W/W |
| 1. Promulgen D | | 3.50 |
| 2. Mineral Oil (65/75 Saybolt) | | 10.000 |
| 3. Lanolin (Cosmetic Grade) | | 1.000 |
| 4. Cetiol V | | 5.000 |
| 5. Propylparabene | | 0.100 |
| 6. Methylparaben | | 0.100 |
| 7. Deionized Water | QS | 100.000 |
| 8. Special Oat Flour | | 1.00 |
| 9. Carbopol 961 | | 0.075 |
| 10. Propylene Glycol | | 5.00 |
| 11. Dowicil 200 | | 0.100 |
| 12. Perfume | | QS |
| 13. Color | | QS |

COMPOUNDING PROCEDURE

Weigh No. 1 - No. 6 into a container and heat while stirring to about 72° C. In a separate container weigh No. 7 and start stirring while adding No. 9. Add No. 8 and No. 10. Continue stirring and heat the aqueous phase ingredients to about 72° C. Add the water phase which should be at a temperature of about 72° C. to the oil phase which should be at the same temperature. Cool to 40° C. and add No. 11 and No. 12 and No. 13. Fill at 25°-30° C.

EXAMPLE 19

| SKIN CARE MOISTURIZING LOTION | ATTRIBUTES: FOR DRY SKIN; NONIONIC, LUBRICATING pH OF APPROXIMATELY 7. | |
|---|---|---|
| INGREDIENT | | % W/W |
| 1. Petrolatum (White USP) | | 10.00 |
| 2. Mineral Oil (65/75 Saybolt) | | 18.00 |
| 3. Myrj 52-5 | | 3.00 |
| 4. Lanolin (Cosmetic Grade) | | 0.75 |
| 5. Methylparaben | | 0.10 |
| 6. Propylparaben | | 0.10 |
| 7. Carbopol 934 | | 0.30 |
| 8. Deionized Water | QS | 100.00 |
| 9. Special Oat Flour | | 1.00 |
| 10. Triethanolamine | | 0.30 |
| 11. Propylene Glycol | | 3.00 |
| 12. Dowicil 200 | | 0.10 |
| 13. Perfume | | QS |
| 14. Color | | QS |

COMPOUNDING PROCEDURE

Weigh No. 1 - No. 6 into a container, commence stirring and heating to 72° C. Weigh No. 8 into a separate container; commence stirring, and No. 7, No. 9 and No. 11. Heat the water phase ingredients to 72° C. and add these to the oil phase ingredients. Add No. 10, continue mixing, cool to 40° C. and add No. 12, No. 13 and No. 14. Fill at 25°–+° C.

EXAMPLE 20

| SKIN CARE HAND AND BODY LOTIN | | ATTRIBUTES: ANIONIC OIL/WATER EMULSION, MOISTURIZING, NON-GREASY, PLEASANT RESIDUAL CHARACTERISTICS. |
|---|---|---|
| INGREDIENT | | % W/W |
| 1. Stearic Acid (Triple pressed) | | 3.00 |
| 2. Stearyl Alcohol | | 0.50 |
| 3. Mineral Oil (65/75 Saybolt) | | 5.00 |
| 4. Methylparaben | | 0.10 |
| 5. Propylparaben | | 0.10 |
| 6. Isopropyl Palmitate | | 1.0 |
| 7. Lanolin (Cosmetic Grade) | | 1.0 |
| 8. Deionized Water | QS | 100.00 |
| 9. Special Oat Flour | | 2.00 |
| 10. Propylene Glycol | | 5.00 |
| 11. Triethanolamine | | 1.00 |
| 12. Dowicil 200 | | 0.10 |
| 13. Perfume | | QS |
| 14. Color | | QS |

COMPOUNDING PROCEDURE

Weight No. 1 - no. 7 and commence heating, while stirring, to about 72° C. Weigh No. 8 into another container and add No. 9 - No. 11; commence heating, while stirring, to 72° C. and at this temperature add this (aqueous emulsion phase) to the oil phase. Cool to 40° C., add No. 12, No. 13 and No. 14. Fill at 25°–30° C.

EXAMPLE 21

| SKIN CARE MOISTURIZING CREAM | | ATTRIBUTES: NONIONIC OIL/WATER EMULSION, MOISTURIZING, APPROXIMATELY NEUTRAL pH. |
|---|---|---|
| INGREDIENT | | % W/W |
| 1. Promulgen | | 4.5 |
| 2. Stearyl Alcohol | | 3.0 |
| 3. Mineral Oil (65/75 Saybolt) | | 15.0 |
| 4. Cetiol V | | 3.0 |
| 5. Propylparaben | | 0.1 |
| 6. Methylparaben | | 0.1 |
| 7. Deionized water | QS | 100.00 |
| 8. Special Oat Flour | | 2.0 |
| 9. Glycerine | | 5.0 |
| 10. Carbopol 961 | | 0.2 |
| 11. Dowicil 200 | | 0.1 |
| 12. Color | | QS |
| 13. Perfume | | QS |

COMPOUNDING PROCEDURE

Weigh ingredients No. 1 - No. 5 into a container; commence heating to about 72° C. while stirring continuously. In another container weigh No. 7 and No. 8, begin stirring, add No. 10, No. 6 and No. 9 and heat to about 72° C. Add the aqueous emulsion phase to the oil phase while stirring continuously. Cool to about 40° C. and add No. 11, No. 12 and NO. 13. Cool to 25°–30° C. and fill.

EXAMPLE 22

| SKIN CARE MOISTURIZING CREAM | | ATTRIBUTES: ANIONIC OIL/WATER EMULSION, MOISTURIZING NON-GREASY. CAN BE USED FOR MASSAGE PURPOSES. |
|---|---|---|
| INGREDIENT | | % W/W |
| 1. Stearic Acid (Triple pressed) | | 3.00 |
| 2. Stearyl Alcohol | | 2.00 |
| 3. Mineral Oil (65/75 Saybolt) | | 7.00 |
| 4. Propylparaben | | 0.10 |
| 5. Methylparaben | | 0.10 |
| 6. Deionized Water | QS | 100.00 |
| 7. Special Oat Flour | | 2.00 |
| 8. Propylene Glycol | | 5.00 |
| 9. Triethanolamine | | 1.00 |
| 10. Dowicil 200 | | 0.10 |
| 11. Perfume | | QS |
| 12. Color | | QS |

COMPOUNDING PROCEDURE

Weigh No. 1, No. 2, No. 3 and No. 4 into a container; commence stirring and heat to 70° C. In another container weigh No. 5, No. 6, No. 7, No. 8 and No. 9; commence stirring while heating to 70°–73° C. Cool to 40° C.; add No. 10, No. 11 and No. 12.

COMPOUNDING PROCEDURE

Add No. 4 to No. 3 and mix until homogeneous. Then add this and No. 4, No. 5 and No. 6 to No. 1. Continue mixing until completely homogeneous. Filling must be accomplished while the batch is stirred continuously.

EXAMPLE 23

| SKIN CARE NIGHT CREAM | ATTRIBUTES: MOISTURIZING, LUBRICATING, PROTECTIVE NONIONIC OIL/WATER EMULSION. | |
|---|---|---|
| INGREDIENT | | % W/W |
| 1. Arlacel 165 | | 5.00 |
| 2. Cetyl Alcohol | | 10.00 |
| 3. Mineral Oil (65/75 Saybolt) | | 25.00 |
| 4. Propylparaben | | 0.10 |
| 5. Silicone Fluid 200/350 Cenistokes (19) | | 0.50 |
| 6. Glycerine | | 5.00 |
| 7. Methylparaben | | 0.10 |
| 8. Special Oat Flour | | 1.50 |
| 9. Deionized Water | QS | 100.00 |
| 10. Dowicil 200 | | 0.10 |
| 11. Perfume | | QS |
| 12. Color | | QS |

EXAMPLE 25

| SKIN CARE WASHABLE CLEANSING CREAM | ATTRIBUTES: OIL/WATER ANIONIC EMULSION: SOLVENT AS WELL AS DISPERSION AND EMULSIFYING CHARACTERISTICS. WASHES OFF EASILY WITH WATER. | |
|---|---|---|
| INGREDIENT | | % W/W |
| 1. Stearic Acid (Triple pressed) | | 4.00 |
| 2. Lanolin (Cosmetic Grade) | | 3.00 |
| 3. Mineral Oil (65/75 Saybolt) | | 10.00 |
| 4. Methylparaben | | 0.10 |
| 5. Propylparaben | | 0.10 |
| 6. Cetyl Alcohol | | 1.20 |
| 7. Deionized Water | QS | 100.00 |
| 8. Special Oat Flour | | 2.00 |
| 9. Triethanolamine | | 1.00 |
| 10. Sipon EC-111 | | 2.00 |
| 11. Perfume | | QS |
| 12. Color | | QS |

COMPOUNDING PROCEDURE

Heat the oil phase (No. 1 - No. 5) to 70°–73° C. while stirring. Heat the aqueous phase (No. 6 - No. 9) to 70°–73° C. while stirring add the aqueous to the oil phase; cool to about 40° C. and add No. 10, No. 11 and No. 12. Fill at 25°–30° C.

COMPOUNDING PROCEDURE

Weigh the "oil" phase of the emulsion (No. 1 - No. 6) into a container; commence heating while stirring to 70°–73° C. In another container weigh the water phase (No. 7 - No. 10), begin heating, while stirring, to 70°–73° C. Add the aqueous phase which should be at this same temperature. Cool to 30° C. and add No. 11 and No. 12. Fill at 25°–30° C.

EXAMPLE 24

| SKIN CARE BATH OIL | ATTRIBUTES: CONDITIONING EFFECTS DUE TO PROTEIN CONTENT OF OAT FLOUR, EMOLLIENT AND LUBRICATING, SPREADING CHARACTERISTICS. MUST BE SHAKEN BEFORE USE. | |
|---|---|---|
| INGREDIENT | | % W/W |
| 1. Mineral Oil (65/75 Saybolt) | QS | 100.00 |
| 2. Isopropyl Myristate | | 20.00 |
| 3. Brij 93 | | 7.00 |
| 4. Perfume | About 2–4% | |
| 5. Special Oat Flour | | 10.00 |
| 6. Color | | QS |

EXAMPLE 26

| SKIN CARE | ATTRIBUTES: NONIONIC OIL/WATER EMULSION, CONTAINS LANOLIN DERIVATIVES, LUBRICATING BUT NON "GREASY". |  |
|---|---|---|
| INGREDIENT | | % W/W |
| 1. Amerchol L101 | | 5.0 |
| 2. Promulgen | | 3.0 |
| 3. Stearyl Alcohol | | 3.0 |
| 4. Mineral Oil (65/75 Saybolt) | | 10.0 |
| 5. Propylparaben | | 0.1 |
| 6. Methylparaben | | 0.1 |
| 7. Deionized Water | QS | 100.00 |
| 8. Special Oat Flour | | 2.0 |
| 9. Glycerine | | 5.0 |
| 10. Dowicil 200 | | 0.1 |
| 11. Perfume | | QS |
| 12. Color | | QS |

COMPOUNDING PROCEDURE

Weigh the "oil" phase (No. 1 - No. 5) into a container, start heating and mixing. Heat to 70°–73° C. Weigh the "water" phase into another container (No. 6 - No. 9) commence heating and stirring. Heat this phase to 70°–73° C. and add to the oil phase which should be at the same temperature. Cool batch while stirring to 30° C. and add No. 10, No. 11 and No. 12. Fill at 25°–30° C.

EXAMPLE 27

| SKIN CARE BUBBLE BATH | ATTRIBUTES: HIGH VISCOSITY, GOOD FOAM CONDITIONING. |  |
|---|---|---|
| INGREDIENT | | % W/W |
| 1. Natrosol 250HR | | 0.500 |
| 2. Deionized Water | QS | 100.000 |
| 3. Special Oat Flour | | 2.000 |
| 4. Methylparaben | | 0.100 |
| 5. Super-Amide L9A | | 3.000 |
| 6. Maprofix NH | | 35.000 |
| 7. Formaldehyde Solution (USP) | | 0.075 |
| 8. Uvinuls DS49 | | 0.075 |
| 9. Perfume | | QS |
| 10. Color | | QS |

COMPOUNDING PROCEDURE

Heat No. 2 70°–73° C.; commence stirring and add No. 1. Mix for about 15 minutes and add No. 3, NO. 4, No. 5 and No. 6. Mix for about 15 minutes after No. 6 has been added. Cool to 40°–43° C. and add No. 7, No. 8, No. 9 and No. 10. Fill at 25°–30° C.

EXAMPLE 28

| SKIN CARE CLEANSING LOTION | ATTRIBUTES: GOOD SOLVENT EFFECT; ALSO EMULSIFICATION AND DISPERSION ATTRIBUTES FOR REMOVAL OF MAKEUP OR ENVIRONMENTAL CONTAMINANTS SUCH AS DUST AND DIRT. |  |
|---|---|---|
| INGREDIENT | | % W/W |
| 1. Promulgen | | 2.50 |
| 2. Mineral Oil (65/75 Saybolt) | | 20.00 |
| 3. Lanolin (Cosmetic Grade) | | 1.00 |
| 4. Isopropyl Myristate | | 5.00 |
| 5. Emcol E607S | | 0.25 |
| 6. Carbitol Solvent | | 0.75 |
| 7. Deionized Water | QS | 100.00 |
| 8. Special Oat Flour | | 2.00 |
| 9. Glycerine | | 5.00 |
| 10. Methylparaben | | 0.10 |
| 11. Propylparaben | | 0.10 |
| 12. Dowicil 200 | | 0.10 |
| 13. Perfume | | QS |

COMPOUNDING PROCEDURE

Weight No. 1, No. 2, No. 3, No. 4, No. 5 and No. 11 into a container and begin heating and stirring. Heat to 70°–73° C. In another container weigh No. 7, No. 8, No. 9 and No. 10; begin heating and stirring. Heat to 70°–73° C. and add the "water" phase of the emulsion to the "oil" phase which should be at the same temperature (both should be at 70°–73° C.). After joining the phases the batch should be cooled to 35°–40° C. at which temperature add No. 12 and No. 13. Fill at 25°–30° C.

EXAMPLE 29

| SKIN CARE CUTICLE CREAM | ATTRIBUTES: MOISTURIZING EMOLLIENT HAS NEUTRAL pH |
|---|---|
| INGREDIENT | % W/W |
| 1. Polawax | 7.50 |
| 2. Stearyl Alcohol | 6.00 |
| 3. Lantrol | 2.00 |
| 4. Mineral Oil (65/75 Saybolt) | 15.00 |
| 5. Cetiol V | 4.00 |
| 6. Isopropyl Palmitate | 2.00 |
| 7. Propylparaben | 0.10 |
| 8. Deionized Water QS | 100.00 |
| 9. Methylparaben | 0.10 |
| 10. Glycerine | 5.00 |
| 11. Special Oat Flour | 2.00 |
| 12. Dowicil 200 | 0.10 |

COMPOUNDING PROCEDURE

Weight the "oil" phase No. 1 - No. 7; begin heating and stirring. Heat to 70°-73° C. Weigh the "water" phase No. 8 - No. 11 and begin heating and stirring. Heat to 70°-73° C. and add the water phase to the oil pahse. Both should be 70°-73° C. Cool to 40° C. and add No. 12. Fill at 25°-30° C.

EXAMPLE 30

| SKIN CARE FRESHENER WITH POWDER RELATED RESIDUAL CHARACTERISTICS | ATTRIBUTES: CONDITINING, COOLING, LEAVES POWDER-LIKE RESIDUE UPON SOLVENT EVAPORATION. |
|---|---|
| INGREDIENT | % W/W |
| 1. Carbopol 940 | 0.20 |
| 2. Deionized Water | 50.00 |
| 3. Ethyl Alcohol SDA No. 40 | 15.00 |
| 4. Special Oat Flour | 3.00 |
| 5. Triethanolamine | 0.20 |
| 6. Methylparaben | 0.10 |
| 7. Allantoin | 0.10 |
| 8. Perfume | QS |
| 9. Color | QS |
| 10. Dowicil 200 | 0.10 |

COMPOUNDING PROCEDURE

Weight No. 2; commence stirring. Slowly add No. 1. When the carbopol has completely hydrated proceed to weigh No. 3, and add No. 6 and No. 7. Stir until these items dissolve and add this to the carbopol water dispersion. Add the remainder of the formulation ingredients while stirring continuously. Stir after the batch has been permitted to age for 12-15 hours and fill.

EXAMPLE 31

| SKIN CARE BATH OIL | ATTRIBUTES: CONDITIONING LUBRICATING MOISTURIZING. CAN BE PACKAGED IN TUBES. |
|---|---|
| INGREDIENT | % W/W |
| 1. Special Oat Flour | 5.0 |
| 2. Cabosil M-5 | 4.0 |
| 3. Tween 80 | 8.0 |
| 4. Myvacet Type 9-40 | 20.0 |
| 5. Mineral Oil (65/75 Saybolt) QS | 100.00 |
| 6. Isopropyl Myristate | 5.0 |
| 7. Perfume | QS |
| 8. Color | QS |

COMPOUNDING PROCEDURE

Weigh all ingredients with the exception of No. 2. Commence stirring. Add No. 2 and stir using a stirrer designed to impart high shearing stress (i.e., propeller type).

EXAMPLE 32

| SKIN CARE ASTRINGENT | ATTRIBUTES: COOLING, HELPS CONDITION AND MOISTURIZE. |
|---|---|
| INGREDIENT | % W/W |
| 1. Deionized Water | 60.00 |
| 2. Laponite XLG | 2.00 |
| 3. Special Oat Flour | 3.00 |
| 4. Chlorhydrol (50%) | 3.00 |
| 5. Ethyl Alcohol (SDA No. 40) | 16.50 |
| 6. Methylparaben | 0.10 |
| 7. Deionized Water QS | 100.00 |

EXAMPLE 32-continued

| SKIN CARE ASTRINGENT | ATTRIBUTES: COOLING, HELPS CONDITION AND MOISTURIZE. |
|---|---|
| INGREDIENT | % W/W |
| 8. Perfume | QS |

COMPOUNDING PROCEDURE

Weigh No. 1 and add while stirring so to impart high shear stress No. 2. After No. 2 has completly dispersed and hydrated, add No. 3, No. 4, No. 5, No. 6, No. 7 and No. 8.

EXAMPLE 33

| SKIN CARE TALC | ATTRIBUTES: LEAVES SMOOTH RESIDUAL FEEL. HELPS CONDITION AND MOISTURIZE THE SKIN. | |
|---|---|---|
| INGREDIENT | | % W/W |
| 1. Talc | QS | 100.00 |
| 2. Magnesium stearate | | 2.5 |
| 3. Zinc Oxide | | 2.0 |
| 4. Special Oat Flour | | 3.0 |
| 5. Perfume | | QS |

COMPOUNDING PROCEDURE

Add No. 2 - No. 5 to No. 1 and blend until completely uniform.

EXAMPLE 34

| HAIR CARE LIQUID SHAMPOO (TRANSLUCENT IN APPEARANCE) | ATTRIBUTES: CONDITIONING AND MANAGEABILITY IMPARTING. | |
|---|---|---|
| INGREDIENT | | % W/W |
| 1. Siponesy | | 30.00 |
| 2. Ninol 2012 Extra | | 6.00 |
| 3. Methylparaben | | 0.10 |
| 4. Versens Regular | | 0.02 |
| 5. Citric Acid (Anhydrous) | | 0.20 |
| 6. Special Oat Flour Dispersion (1% in deionized water) | | 50.00 |
| 7. Deionized Water | QS | 100.00 |
| 8. Formalin USP | | 0.075 |
| 9. Perfume | | QS |
| 10. Color | | QS |

COMPOUNDING PROCEDURE

Heat No. 1 - No. 7 to approximately 60° C. while stirring continuously. Cool to 40° C. and add No. 8, No. 9 and No. 10.

EXAMPLE 35

| HAIR CARE LIQUID SHAMPOO (PEARLESCENT IN APPEARANCE) | ATTRIBUTES: CONDITIONING, MANAGEABILITY IMPARTING |
|---|---|
| INGREDIENT | % W/W |
| 1. Standapol WA Special | 35.00 |
| 2. Ninol 128 Extra | 5.00 |
| 3. Ethylene glycol monostearate | 2.50 |
| 4. Methylparaben | 0.10 |
| 5. Citric Acid | 0.10 |
| 6. Special Oat Flour Dispersion (4% in deionized water) | 50.00 |
| 7. Perfume | QS |
| 8. Formalin USP | 0.075 |
| 9. Color | QS |
| 10. Deionized Water | 100.00 |

COMPOUNDING PROCEDURE

Heat while continuously stirring No. 1 - No. 6 to approximately 80° C.; cool to approximately 40° C. and add No. 7, No. 8, No. 10 and No. 9.

EXAMPLE 36

HAIR CARE GEL SHAMPOO (TRANSLUCENT IN APPEARANCE)

ATTRIBUTES: CONDITIONING, MANAGEABILITY IMPARTING.

| INGREDIENT | % W/W |
|---|---|
| 1. Maprofix TLS | 30.00 |
| 2. Ninol 128 Extra | 8.00 |
| 3. Natrosol 250HR | 1.00 |
| 4. Special Oat Flour (2% dispersion in deionized water) | 50.00 |
| 5. Versene Regular | 0.05 |
| 6. Methylparaben | 0.10 |
| 7. Perfume | QS |
| 8. Color | QS |
| 9. Deionized Water | |
| 10. Formalin Solution USP | 0.075 |

COMPOUNDING PROCEDURE

Heat No. 4, while stirring, to approximately 70° C. and add No. 3 while stirring continuously. Cool to approximately 40° C. and add Nos. 1, 2, 5, 6, 7, 8, No.9 and 10.

EXAMPLE 37

HAIR CARE GEL SHAMPOOL (PEARLESCENT IN APPEARANCE)

ATTRIBUTES: EXCELLENT FOAM CHARACTERISTICS. CONDITIONING IMPARTS LUSTER AND MANAGEABILITY.

| INGREDIENT | | % W/W |
|---|---|---|
| 1. Stepanol WA Special | | 25.0 |
| 2. Steol 4N | | 25.0 |
| 3. Ninol 128 Extra | | 6.0 |
| 4. Methylparaben | | 0.1 |
| 5. Propylparaben | | 0.1 |
| 6. Ethylene glycol monostearate | | 2.0 |
| 7. Deionized Water | QS | 100.00 |
| 8. Special Oat Flour | | 1.0 |
| 9. Citric Acid | QS to pH 7.0 | |
| 10. Formaldehyde Solution USP | | 0.075 |
| 11. Perfume | | QS |
| 12. Colors | | QS |

COMPOUNDING PROCEDURE

Weigh No. 1 - No. 8 into a container and heat, while stirring carefully to avoide aeration, to 70°–73° C. Mix for 15 minutes at 70°–73° C. and cool to 35°–40° C at which temperature No. 9, No. 10, No. 11 and No. 12 should be added.

EXAMPLE 38

HAIR CARE CREAM SHAMPOO

ATTRIBUTES: CONDITIONING AND MANAGEABILITY IMPARTING SMOOTH PASTE WITH EXCELLENT WATER DISPERSION CHARACTERISTICS AND FOAM.

| INGREDIENT | | % W/W |
|---|---|---|
| 1. Stearic Acid (Triple pressed) | | 1.000 |
| 2. Sodium hydroxide USP | | 1.000 |
| 3. Cetyl Alcohol (NF Grade) | | 2.000 |
| 4. Lanamine | | 5.000 |
| 5. Special Oat Flour | | 1.000 |
| 6. Deionized Water | QS | 100.000 |
| 7. Methylparaben | | 0.100 |
| 8. Standapol WAQ Special | | 60.000 |
| 9. Perfume | | QS |
| 10. Color | | QS |
| 11. Formalin Solution USP | | .075 |

COMPOUNDING PROCEDURE

Dissolve No. 2 in No. 6 while blending and heating No. 1, No. 3 and No. 4 to about 62° C. Add the sodium hydroxide solution to the No. 1, No. 3 and No. 4 mixture. Continue stirring and weigh No. 5 - No. 8, while stirring, and add this to the heated emulsion. Continue mixing (avoid air entrapment) while permitting the batch to cool to 28° C. at which time add No. 9, No. 10 and No. 11.

EXAMPLE 39

| HAIR CARE CREAM RINSE WITH OAT FLOUR | | ATTRIBUTES: MAKES HAIR SOFT, LUSTEROS AND MANAGEABLE WHILE IMPARTING CONDITIONING ATTRIBUTES. |
|---|---|---|
| INGREDIENT | | % W/W |
| 1. Polawax | | 1.0 |
| 2. Arquad 2HT75 | | 2.0 |
| 3. Cetyl Alcohol (N.F.) | | .2.0 |
| 4. Ceralan | | 0.5 |
| 5. Propylparaben | | 0.05 |
| 6. Deionized Water | QS | 100.00 |
| 7. Propylene Glycol | | 2.0 |
| 8. Special Oat Flour | | 2.0 |
| 9. Methylparaben | | 0.1 |
| 10. Perfume | | QS |
| 11. Color | | QS |

COMPOUNDING PROCEDURE

Heat No. 1 - No. 5 to about 72° C. while stirring continuously. In another container heat No. 6 - No. 9 to about 72° C. Add the aqueous phase (No. 6 - No. 9) which should be at 72° C. to the oil phase No. 1 - No. 5. Cool the batch, while stirring continuously to 30° C. and add No. 10 and No. 11. Fill at 25°–30° C.

EXAMPLE 40

| HAIR CARE HAIR CONDITIONER LOTION | | ATTRIBUTES: SOFTENS AND CONDITIONS, WORKS IN ONE OR TWO MINUTES. |
|---|---|---|
| INGREDIENT | | % W/W |
| 1. Polawax | | 3.00 |
| 2. Stearyl Alcohol | | 1.00 |
| 3. Emcol E607S | | 1.00 |
| 4. Lanolin (Cosmetic Grade) | | 0.25 |
| 5. Mineral Oil (65/75 Saybolt) | | 2.00 |
| 6. Deionized Water | QS | 100.00 |
| 7. Special Oat Flour | | 2.00 |
| 8. Propylene Glycol | | 2.00 |
| 9. Methylparaben | | 0.10 |
| 10. Perfume | | QS |
| 11. Color | | QS |

COMPOUNDING PROCEDURE

Heat the "oil phase" (No. 1 - No. 5) to about 72° C. while stirring continuously. Heat the aqueous phase (No. 6 - No. 9) to 70°–73° C. while stirring continuously. Add the aqueous phase to the oil phase, both should be at 70°–73° C., while stirring continuously. Cool to 30° C. and add No. 10 and No. 11. Fill at 25°–30° C.

EXAMPLE 41

| HAIR CARE HAIR CONDITIONING CREAM | | ATTRIBUTES: NONIONIC/CATIONIC EMULSION, RAPID CONDITIONING, SOFTENING, IMPARTS HIGH LUSTER. |
|---|---|---|
| INGREDIENT | | % W/W |
| 1. Promulgen | | 4.00 |
| 2. Mineral Oil (65/75 Saybolt) | | 5.00 |
| 3. Cetiol V | | 3.00 |
| 4. Grape seed oil | | 4.00 |
| 5. Stearyl Alcohol | | 4.00 |
| 6. Propylparaben | | 0.10 |
| 7. Ammonyx No. 4 (22) | | 4.00 |
| 8. Propylene Glycol | | 5.00 |
| 9. Deionized Water | QS | 100.00 |
| 10. Sorbic Acid | | 0.20 |
| 11. Methylparaben | | 0.10 |
| 12. Special Oat Flour | | 2.00 |

COMPOUNDING PROCEDURE

Weigh No. 1, No. 2, No. 3, No. 4, No. 5 and No. 6 into a container, commence stirring and heating. Heat to 70°–73° C. Weigh No. 7, No. 8, No. 9, No. 10, No. 11 and No. 12 into another container, commence stirring and heating. Heat to 70°–73° C. and add to the (No. 1 - No. 6) mixture which should also be at 70°–73° C. Cool to 25°–30° C. and fill.

EXAMPLE 42

| HAIR CARE SETTING SYSTEM | ATTRIBUTES: CONDITIONING, IMPARTS LUSTER, MANAGEABILITY AND GOOD HOLDING UNDER HUMID CONDITIONS. OAT FLOUR USED AS A PLASTICIZER AND CONDITIONER. | |
|---|---|---|
| INGREDIENT | | % W/W |
| 1. Gantrez 225 | | 3.5 |
| 2. Ethyl Alcohol SDA No. 40 | QS | 100.00 |
| 3. Special Oat Flour (1% dispersion in deionized water) | | 10.0 |
| 4. Diisopropanolamine | | 0.2 |
| 5. Perfume | | QS |

COMPOUNDING PROCEDURE

Weigh item No. 2 and begin stirring. Add No. 1 and mix until the dispersion is clear and homogeneous. Add No. 3, No. 4 and No. 5. Mix until the dispersion is uniform.

EXAMPLE 43

| HAIR CARE HAIR CONDITIONER | ATTRIBUTES: SETTING CHARACTERISTICS, CONDITIONING IMPARTS MANAGEABILITY, LUSTER AND TEXTURE. |
|---|---|
| INGREDIENT | % W/W |
| 1. Resyn 28-2930 | 2.00 |
| 2. Ammonium Hydroxide (28% Solution) | 0.120 |
| 3. Ethoxylan 50 | 0.25 |
| 4. Perfume | QS |
| 5. Ethyl Alcohol (SDA No. 40) | 45.00 |
| 6. Special Oat Flour (1% dispersion in deionized water) | 51.78 |
| 7. Panthenol | 0.5 |
| 8. Formaldehyde Solution USP | 0.075 |
| 9. Color | QS |

COMPOUNDING PROCEDURE

Weigh No. 5 and add, while stirring continuously, No. 1, No. 2, No. 3, No. 4, No. 6, No. 7, No. 8 and No. 9. Mix until a completely uniform dispersion results. Filter through 100 mesh or greater.

EXAMPLE 44

| SKIN CARE BABY POWDER | ATTRIBUTES: THE INCLUSION OF OAT FLOUR IMPARTS GOOD ADHESION TO THE EPIDERMIS, WATER ADSORBING CHARACTERISTICS AND THE DERMATOLOGICAL ATTRIBUTES RELATED TO OAT FLOUR. THE POWDER LEAVES THE SKIN DRY SOFT AND SMOOTH TO THE TOUCH. | |
|---|---|---|
| INGREDIENT | | % W/W |
| 1. Talc | QS | 100.00 |
| 2. Magnesium Stearate | | 2.00 |
| 3. Syloid No. 72 | | 1.00 |
| 4. Ottasept Extra | | 0.10 |
| 5. Special Oat Flour | | 10.00 |
| 6. Perfume | | QS |

COMPOUNDING PROCEDURE

Add ingredients No. 2 through No. 6 to the talc; blend until uniform.

EXAMPLE 45

| SKIN CARE FOOT POWDER | ATTRIBUTES: EPIDERMAL EMOLLIENCY NATURAL PROTEIN, DERMATOLOGICAL RELATED BENEFITS CONSISTENT WITH THE USE OF OAT FLOUR. THE POWDER CONTAINS A PERSPIRATION INHIBITING MATERIAL AS WELL AS BEING DEODORANT. | |
|---|---|---|
| INGREDIENT | | % W/W |
| 1. Talc | QS | 100.00 |

EXAMPLE 45-continued

| SKIN CARE FOOT POWDER | ATTRIBUTES: EPIDERMAL EMOLLIENCY NATURAL PROTEIN, DERMATOLOGICAL RELATED BENEFITS CONSISTENT WITH THE USE OF OAT FLOUR. THE POWDER CONTAINS A PERSPIRATION INHIBITING MATERIAL AS WELL AS BEING DEODORANT. |
|---|---|

| INGREDIENT | % W/W |
|---|---|
| 2. Special Oat Flour | 10.00 |
| 3. Microdry | 5.00 |
| 4. Zinc Oxide | 2.00 |
| 5. Syloid 72 | 2.00 |
| 6. Perfume | QS |

COMPOUNDING PROCEDURE

Add No. 2 through No. 6 to No. 1 and blend until uniform.

EXAMPLE 46

| SKIN CARE BODY TALC WITH ANTIPERSPIRANT QUALITIES | ATTRIBUTES: OAT FLOUR OFFERS A SOURCE OF NATURAL PROTEIN AND EMOLLIENT LIPIDS. OAT FLOUR HAS BEEN USED TO RELIEVE A NUMBER OF DERMATOLOGICAL CONDITONS OF BOTH A SPECIFIC AND NON-SPECIFIC NATURE SUCH AS PRURITUS, DRYNESS AND CHAPPING. THE POWDER HAS INGREDIENTS TO HELP SUPPRESS PERSPIRATION AND OFFER A DEODORANT EFFECT. |
|---|---|

| INGREDIENT | | % W/W |
|---|---|---|
| 1. Talc | QS | 100.00 |
| 2. Microdry | | 3.00 |
| 3. Syloid No. 72 | | 2.00 |
| 4. Special Oat Flour | | 10.00 |
| 5. Perfume | | QS |

COMPOUNDING PROCEDURE

Add No. 2 through No. 5 to No. 1 and mix until completely uniform.

EXAMPLE 47

| SKIN CARE BABY POWDER | ATTRIBUTES: OAT FLOUR PROVIDES POTENTIAL DERMATOLOGICAL-RELATED ATTRIBUTES, NATURAL PROTEIN, EMOLLIENT LIPIDS. LEAVES SKIN SOFT AND VELVETY SMOOTH TO THE TOUCH. |
|---|---|

| INGREDIENT | % W/W |
|---|---|
| 1. Talc | 90.15 |
| 2. Zinc Stearate | 2.50 |
| 3. Syloid No. 72 | 2.00 |
| 4. Special Oat Flour | 3.00 |
| 5. Zinc Oxide | 2.00 |
| 6. Dioxin | 0.10 |
| 7. Perfume | QS |

COMPOUNDING PROCEDURE

Add ingredients No. 2 through No. 7 to the talc; blend until completely uniform.

EXAMPLE 48

| | |
|---|---|
| SKIN CARE FOOT POWDER | ATTRIBUTES: OAT FLOUR OFFERS CONDITIONING THROUGH NATURAL PROTEIN; GOOD ADHERENCE TO THE SKIN. THE FORMULATION ALSO ACTS AS A DEODORANT, AND CONTAINS AN AGENT TO REDUCE PERSPIRATION. |

| INGREDIENT | % W/W |
|---|---|
| 1. Talc | 82.65 |
| 2. Special Oat Flour | 3.00 |
| 3. Microdry | 10.00 |
| 4. Syloid 72 | 2.00 |
| 5. Ottasept Extra | 0.15 |
| 6. Zinc Oxide | 2.00 |
| 7. Perfume | QS |

COMPOUNDING PROCEDURE

Add No. 2 through No. 7 to No. 1 and blend until uniform.

EXAMPLE 49

| | |
|---|---|
| SKIN CARE DEODORANT BODY POWDER | ATTRIBUTES: OAT FLOUR OFFERS NATURAL PROTEIN, AND EMOLLIENT LIPIDS. GOOD ADHERENCE TO THE SURFACE OF THE EPIDERMAL LAYER. LEAVES THE SKIN SOFT, AND SMOOTH TO THE TOUCH. |

| INGREDIENT | % W/W |
|---|---|
| 1. Talc | 80.75 |
| 2. Zinc Stearate | 6.00 |
| 3. Syloid 72 | 2.00 |
| 4. Special Oat Flour | 3.00 |
| 5. Titanium Dioxide | 2.00 |
| 6. Ottasept Extra | 0.25 |
| 7. Perfume | QS |
| 8. Magnesium Carbonate | 3.00 |

COMPOUNDING PROCEDURE

Add No. 2 through No. 8 to No. 1 and blend until the ingredients are uniformly dispersed.

EXAMPLE 50

| | |
|---|---|
| SKIN CARE BODY TALC WITH DEODORANT AND ANTIPERSPIRANT CHARACTERISTICS | ATTRIBUTES: OAT FLOUR PROVIDES WHOLE PROTEIN AND LIPIDS FOR SKIN CONDITIONING AND EMOLLIENCY. PERSPIRATION INHIBITING AND DEODORANT EFFECT PROVIDED BY ALUMINUM SALT. |

| INGREDIENT | % W/W |
|---|---|
| 1. Talc | 83.50 |
| 2. Special Oat Flour | 3.50 |
| 3. Microdry | 7.50 |
| 4. Syloid 72 | 3.00 |
| 5. Ottosept Extra | 0.15 |
| 6. Aluminum Stearate | 2.00 |
| 7. Perfume | QS |

COMPOUNDING PROCEDURE

Add ingredients No. 2 through No. 7 to the talc. Blend until the formulation is completely uniform.

EXAMPLE 51

| | |
|---|---|
| SOAP | THE SOAP CONTAINING SPECIAL OAT FLOUR IMPARTS MOISTURIZING AND EMOLLIENT QUALITIES AS WELL AS PROTEIN AND LIPIDS. |

| INGREDIENT | PARTS BY WEIGHT |
|---|---|
| 1. Olive oil (Refined) | 200.00 |
| 2. Stearic Acid (Triple pressed) | 100.00 |
| 3. Corn Oil | 100.00 |
| 4. Oleic Acid | 100.00 |

EXAMPLE 51-continued

| SOAP | THE SOAP CONTAINING SPECIAL OAT FLOUR IMPARTS MOISTURIZING AND EMOLLIENT QUALITIES AS WELL AS PROTEIN AND LIPIDS. |
|---|---|
| INGREDIENT | PARTS BY WEIGHT |
| 5. Butylated Hydroxyanisole | 0.15 |
| 6. Sodium Hydroxide USP | 100.00 |
| 7. Deionized Water | 100.00 |
| 8. Deionized Water | 650.00 |
| 9. Special Oat Flour | 150.00 |
| 10. Perfume | QS |
| 11. Color | QS |

COMPOUNDING PROCEDURE

Heat No. 8 to 75° C. ± 3° C. and sprinkle in No. 9 while mixing with a high shear propeller type stirrer. Heat No. 1 - No. 5 to 92° C. ± 2° C. while stirring slowly to prevent air entrapment. Dissolve No. 6 and No. 7. While maintaining the "oil" mixture at 92° C. ± 2° C. slowly add aliquots of the special oat flour dispersion and sodium hydroxide solution, alternating between the oat flour and sodium hydroxide. Maintain the temperature for one hour after completing the addition of oat flour and sodium hydroxide while continuing to slowly stir the batch. Cool to 68° C. ± 2° C. and add No. 10 and No. 11. Continue cooling to about 25° C. This product can be processed, to remove excess moisture, by applying a vacuum during the compounding operation. The product can also be warmed to about 45° C. for 24 hours prior to pressing to facilitate moisture removal.

Table I

| IDENTIFICATION OF TRADE OR GENERIC LISTED FORMULATION MATERIALS | |
|---|---|
| Trade or Generic Name | Identification |
| 1. Allantoin | 5-Ureidohydantoin |
| 2. Amerchol L101 | Extract of Lanolin Sterols and complex higher Alcohols in their free form |
| 3. Amerlate P | Isopropylester of Normal Branched Chain and Hydroxy Acids of Lanolin |
| 4. Ammonyx 4 | Stearyl Dimethyl Benzyl Ammonium Chloride |
| 5. Arlacel 165 | Glycerol Monostearate and Polyoxyethylene Stearate |
| 6. Arquad 2HT75 | Dialkyl (Tallow) Quaternary Ammonium Salts |
| 7. Beewax | Largely Myricyl Palmitate, Cerotic Acid and Esters and some high Carbon Paraffins |
| 8. Boraxz | Sodium Borate |
| 9. Brij 93 | Polyoxyethylene Oleyl Ether |
| 10. Cab-O-Sil M-5 | Fumed Silica |
| 11. Carbitol Solvent | Diethylene Glycol Monoethyl Ether |
| 12. Carbopol | Carboxyvinyl Polymer |
| 13. Ceralan | Lanolin Alcohols |
| 14. Ceresin Wax | Purified Ozocerite, Mineral Wax |
| 15. Cetiol V | Decyl Oleate |
| 16. Chlorhydrol | Aluminum Chlorohydroxide |
| 17. Chromalite Dark Blue | Ironoxide Pigment |
| 18. Chromalite Magenta | Ironoxide Pigment |
| 19. D&C Red No. 7 | Calcium Salt of 4(O-Sulfo-P-Tolyl-AZO) 3-Hydroxy-2 Naphtholic Acid |
| 20. D&C Red No. 19 | 3-Ethochloride of 9-O-Carboxyphenyl-6-Diethylamino-3-Ethylamino-3-Isoxanthene |
| 21. D&C Red No. 21 | 2,4,5,7 Tetrabromo-3-6 Fluorandiol |
| 22. Dowacil 200 | Cis Isomer of 1-(3 Chloroallyl) 3,5,7, Tria ZA 1-Azoniaadamantane Chloride |
| 23. Emcol E607S | Stearoyl N. Colaminoformyl Methyl Pyridinium Chloride |
| 24. Emerwax 4266-D | Mixture of Higher Fatty Acid and Alcohol Esters and Alcohols (Cetyl, Palmitate Cetyl Alcohol Lauric Stearic and Myristic Acid Esters) |
| 25. Fluid E370 | Polyalkylene Glycol |
| 26. Fullers Earth | Colloidal Aluminum Silicate |
| 27. Gantrez 225 | Monoethyl Ester of Polymethylvinyl Ether/Maleic Acid |
| 28. Gelvatol 3/90 | Polyvinyl Alcohol/Acetate |
| 29. Lanamine | Lanolin Acid Amine |
| 30. Lanolin | Mainly Cholesterol Esters of Higher Fatty Acids |
| 31. Lantrol | Dewaxed Lanolin |
| 32. Laponite XLG | Synthetic Inorganic Silicate with Structural Characteristics Similar to Hectorite, Bentonite or Mont- |

Table I-continued
IDENTIFICATION OF TRADE OR GENERIC LISTED FORMULATION MATERIALS

| Trade or Generic Name | Identification |
|---|---|
| | morillonite |
| 33. Lo Micron Pink 2511 | Ironoxide Pigment |
| 34. Lo Micron Yellow 2576 | Ironoxide Pigment |
| 35. Lo Micron Brown 2593 | Ironoxide Pigment |
| 36. Maprofix NH | Ammonium Lauryl Sulfate |
| 37. Maprofix TLS | Triethanolamine Lauryl Sulfate |
| 38. Methylparaben | Methyl Para Hydroxybenzoate |
| 39. Myrj 52.5 | Polyoxyethylene Stearate |
| 40. Myvacet Type 9–40 | Distilled Acetylated Monoglycerides |
| 41. Natrosol 250HR | Hydroxyethylcellulose |
| 42. Ninol 128 Extra Condensate | Coconut Fatty Acid Diethanolamine |
| 43. Ninol 2012 Extra | Coconut Fatty Acid Diethanolamine Condensate |
| 44. Pearl Glow | Bixmuth Oxychloride |
| 45. Polawax | Polyoxyethylene Lanolin Wax |
| 46. Promulgen | Polyoxyethylene glycol complex of higher molecular weight naturally occurring saturated fatty alcohols |
| 47. Propylparaben | Propylpara Hydroxybenzoate |
| 48. Red No. 2513 | Ironoxide Pigment |
| 49. Resyn 2260 | Acrylic Copolymer Latex |
| 50. Resyn 28–2930 | Carboxylated Vinyl Acetate Terpolymer |
| 51. Silicone Fluid 200/350 Centistokes | Dimethyl Siloxane Polymer |
| 52. Sipon EC-111 | Sodium Cetyl/Stearyl Sulfate |
| 53. Sipon ESY | Sodium Lauryl Ether Sulfate |
| 54. Sorbitol | Hexahydric Alcohol |
| 55. Standamid SD | Coconut Fatty Acid Diethanolamide |
| 56. Standapol SH100 | Anionic Dibasic Acid Monoester Sodium Salt |
| 57. Standapol WA Special | Sodium Lauryl Sulfate |
| 58. Standapol WAQ Special | Sodium Lauryl Sulfate |
| 59. Steol 4N | Sodium Lauryl Ether Sulfate |
| 60. Stepanol WA Special | Sodium Lauryl Sulfate |
| 61. Super Amide L9A | Lauric Acid Diethanolamine Condensate |
| 62. Talc | Hydrous Magnesium Silicate |
| 63. Tween No. 80 | Polyoxyethylene Sorbitan Monooleate |
| 64. Ultra Blue 3585 | Ironoxide Pigment |
| 65. Uvinul DS No. 49 | Sodium Salt of Sulfonated 2-Hydroxy-4-Methoxy - Benzophenone |
| 66. Veegum | Colloidal Magnesium Aluminum Silicate |
| 67. Versene Regular | Ethylene Diaminetetraacetic Acid |
| 67. Versene Regular | Ethylene Diaminetetraacetic Acid (Tetra Sodium Salt) |
| 68. Viscolan | Dewaxed Liquid Lanolin |
| 69 Yellow 2576 | Ironoxide Pigment |

Those modifications and equivalents which fall within the spirit of the invention are to be considered a part thereof.

What is claimed is:

1. A liquid cosmetic preparation comprising a colloidally stable dispersion of oat flour having a particle size such that at least about 98% thereof passes through a 200 mesh screen (U.S. Sieve Series) in a liquid vehicle, said oat flour being employed in an amount of from about 1 to 20% by weight of the preparation.

2. A cosmetic preparation in accordance with claim 1 in which water and alcohol are present in the liquid vehicle.

3. A cosmetic preparation in accordance with claim 1 in which the liquid vehicle is an oil-in-water emulsion.

4. A cosmetic preparation in accordance with claim 1 in which the liquid vehicle is a water-in-oil emulsion.

5. A cosmetic preparation in accordance with claim 1 in which the oat flour on a dry basis has a protein content of not more than about 16% and a starch content of not less than about 70%.

* * * * *